United States Patent [19]  [11]  3,932,657
Rahman  [45] Jan. 13, 1976

[54] LIPOSOME ENCAPSULATION OF CHELATING AGENTS

[75] Inventor: Yueh Erh Rahman, Downers Grove, Ill.

[73] Assignee: The United States of America as represented by the United States Energy Research and Development Administration, Washington, D.C.

[22] Filed: Nov. 12, 1973

[21] Appl. No.: 415,077

[52] U.S. Cl. ............................... 424/319; 424/365
[51] Int. Cl.² ................ A61K 31/195; A61K 47/00
[58] Field of Search ........................... 424/319, 365

[56] References Cited
OTHER PUBLICATIONS

Rahman et al. — Chem. Abst. Vol. 79, (1973), p. 49585q.
Inchema — Chem. Abst., Vol. 79, (1973), p. 45830t.

Primary Examiner—Sam Rosen
Attorney, Agent, or Firm—John A. Horan; Arthur A. Churm; Robert J. Fisher

[57] ABSTRACT

A method for transferring a chelating agent across a cellular membrane by encapsulating the charged chelating agent within liposomes and carrying the liposome-encapsulated chelating agent to the cellular membrane where the liposomes containing the chelating agent will be taken up by the cells, thereby transferring the chelating agent across the cellular membrane. A chelating agent can be introduced into the interior of a cell of a living organism wherein the liposomes will be decomposed, releasing the chelating agent to the interior of the cell. The released chelating agent will complex intracellularly deposited toxic heavy metals, permitting the more soluble metal complex to transfer across the cellular membrane from the cell and subsequently be removed from the living organism.

9 Claims, 2 Drawing Figures

LEGEND:
- ☐ CONTROL
- ▨ NON-ECAPSULATED DTPA
- ▧ ENCAPSULATED DTPA
- ▩ BOTH

LIPOSOME ENCAPSULATION OF CHELATING AGENTS

CONTRACTUAL ORIGIN OF THE INVENTION

The invention described herein was made in the course of, or under, a contract with the UNITED STATES ATOMIC ENERGY COMMISSION.

BACKGROUND OF THE INVENTION

Heavy metal poisoning is a serious medical problem which has received even more emphasis in recent years since toxic heavy metals such as lead and mercury may very easily enter the body as a consequence of accidents or environmental pollution. Of even more concern are radioactive toxic heavy metals which pose an additional problem due to their radioactivity. The ionizing radiations of the radioactive metals are of even greater concern than their chemical toxicity because of the risk of tumor induction from the radioactive ionization. Toxic heavy metals are known to concentrate in various organs of the body. Plutonium, for example, usually deposits in the liver, it being known that as much as 30 to 60% of an administered amount of plutonium will deposit in the liver. The toxic heavy metal, plutonium in this example, remains in the organ and is only very slowly removed, thereby increasing the potential for tumors.

In the past, the polyaminopolycarboxylic acid, ethylene-diaminetetraacetic acid (EDTA) has been used as a chelating agent for removing toxic metals from animal tissue. More recently, a related polyaminopolycarboxylic acid, diethylenetriaminepentaacetic acid (DTPA) has been shown to have a greater ability to remove various heavy metals. The use of chelating agents for the removal of toxic heavy metals is based on their ability to form stable, nonionic, soluble and readily excretable complexes with the metal molecules in the tissues. They have proven valuable because they, in themselves, have a very low toxicity, are able to form soluble, excretable metal chelates within a body, and resist degradation by cell metabolites. However, a serious limitation for the use of chelating agents is that they exist as hydrated anions in the blood plasma. These anions are unable to penetrate cellular membranes. Therefore, only extracellularly deposited toxic metals can be complexed by the chelating agents and removed from the body, whereas intracellularly deposited metals are not complexed by the chelating agent and therefore are not readily removed. Attempts have been made in the past to increase the penetration of chelating agents through cellular membranes such as by the esterification of polyaminopolycarboxylic acids, but these efforts have met with limited success because of the insolubility and toxicity of the esterified compounds.

It is an object of the present invention to provide a method for transferring a chelating agent across a cellular membrane.

Another object of the present invention is to provide a means for introducing a chelating agent into the interior of a cell.

It is another object of the present invention to provide a method for introducing a chelating agent into the interior of a cell of a living organism by introducing the chelating agent to the organism and carrying it to the cell in the blood stream.

Another object of the present invention is to provide a method for the removal of intracellularly deposited toxic heavy metals.

Still another object of the present invention is to provide a therapy method for toxic heavy metal poisoning whereby both intracellularly deposited toxic heavy metals as well as extracellularly deposited toxic heavy metals can be removed from the body.

SUMMARY OF THE INVENTION

This invention relates to a method for transferring a chelating agent across a cellular membrane by encapsulating the charged chelating agent within liposomes and carrying the liposome encapsulated chelating agent to the cellular membrane where the liposomes containing the chelating agent will be taken up by the cell, thereby transferring the chelating agent across the cellular membrane. The encapsulation of the chelating agent within liposomes permits the introduction of the chelating agent to the interior of the cell wherein the liposomes decompose and release the chelating agent to the interior of the cell. The encapsulated chelating agent can be introduced to the interior of a cell of a living organism by injecting a saline suspension of the liposome encapsulated chelating agent into the blood system of the living organism whereby the chelating agent will be carried to the cell within the blood system. The encapsulation of the chelating agent within liposomes permits removal of intracellularly deposited toxic heavy metals since the liposome encapsulated chelating agent will be passed through the cell wall into the interior of the body cell where the liposome will be biologically degraded by enzymes thereby releasing the chelating agent to the interior of the cell which permits complexing of the toxic heavy metal. The complexed toxic heavy metal can then pass through the cell wall into the blood stream and be removed from the body by normal body processes. The method can be adapted to a therapy method for toxic heavy metal poisoning wherein some of the toxic heavy metals will be deposited within the cells and cannot be removed by other known therapy methods. A suspension of the liposome encapsulated chelating agent is formed in a saline containing nonencapsulated chelating agent and the combined suspension is introduced into the blood stream by intravenous injection. This permits complexing of intracellularly deposited toxic heavy metals as well as complexing of free toxic heavy metals and removal of the so-complexed toxic heavy metals from the body.

BRIEF DESCRIPTION OF THE DRAWINGS

Other objects and advantages of the present invention will become apparent upon reading the following description of the invention and with reference to the drawings in which.

DESCRIPTION OF THE INVENTION

Figure 1:
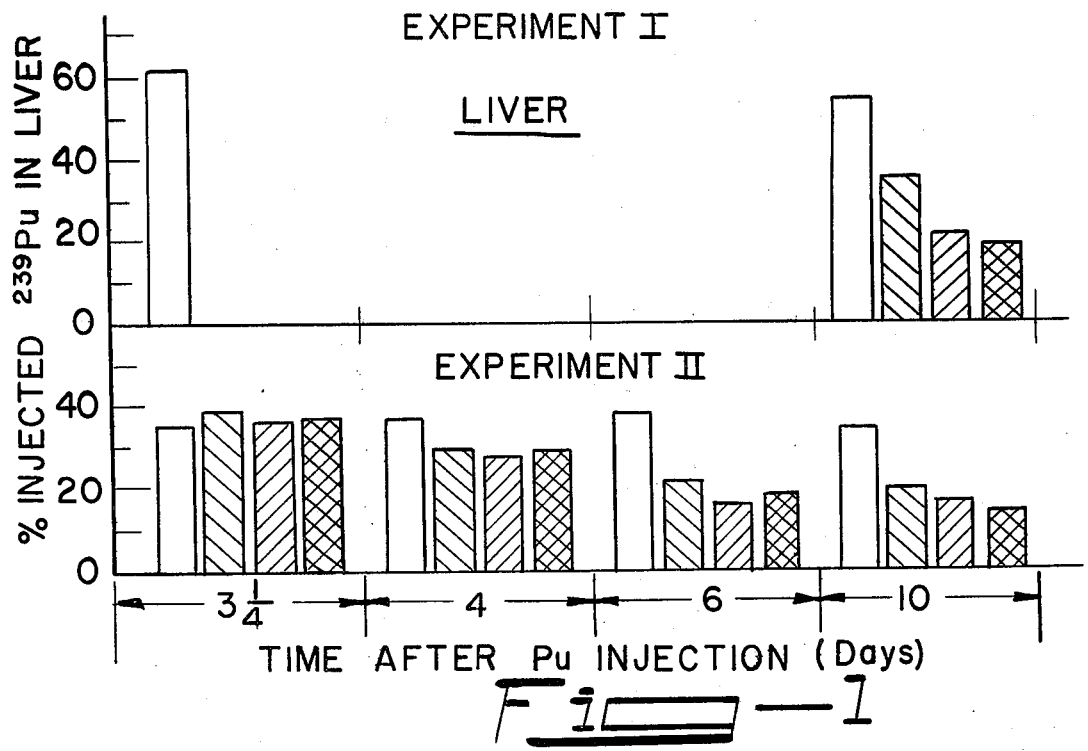
FIG. 1 graphically illustrates the amount of $^{239}$Pu remaining in the liver after intervals of time following various treatments.

In accordance with the present invention, a chelating agent is encapsulated within liposomes to enable transfer of the chelating agent across a cellular membrane. Since toxic heavy metals are known to deposit intracellularly as well as extracellularly, a method for transferring the toxic heavy metal from the interior of the cell is necessary to insure complete removal of toxic heavy metals from the body. While chelating agents are known to be useful in removing extracellularly deposited toxic heavy metals, chelating agents have not heretofore been demonstrated to be efficient in removing intracellularly deposited toxic heavy metals. It is believed that the large negative charge on the chelating ion prevents transfer of the chelating agent across the cellular membrane to the interior of the cell and, therefore, the chelating agent has no effect on intracellularly deposited toxic heavy metals.

One of the reasons toxic heavy metal poisoning, in particular, radioactive toxic heavy metals, are of such concern is the fact that these metals concentrate selectively in vital organs, such as the liver and spleen. It has been found that the metal, such as colloidal plutonium in the liver, is associated mainly, if not solely, with lysosomes. The lysosomes are the usual location for matters foreign to the organism ingested by cells including the heavy metals. Liposomes injected into the body also will be directed to and later found in the lysosomes. The term "liposomes" as used herein refers to artificial spherules formed by thin layers of phospholipid in the presence of any electrolyte. Phospholipids when placed in an electrolytic solution form concentric bimolecular lipid layers separated by the entrapped aqueous compartments. It can be seen then that the liposomes are composed of concentric bimolecular layers of lipid alternating with aqueous layers.

It has been found that polyaminopolyccarboxylic acid chelating agents, EDTA and DTPA in particular, can be encapsulated in liposomes. A lipid mixture is dried to form a thin film on the walls of a flask. A solution of the electrolyte is introduced into the flask and the thin film of lipid is wetted with the solution. The contents of the flask are then shaken, whereby small spherules will be formed. The small spherules are composed of lipid layers separated by entrapped aqueous layers, and are herein referred to as liposomes. The liposomes thus formed will have encapsulated layers of the electrolyte, in the present instances the electrolyte being a chelating agent.

As an example, liposomes were prepared from a 3 to 1 mixture of phosphatidylcholine, egg lecithin, and cholesterol dissolved in chloroform. In the present instance, 4.5 mg egg lecithin and 1.5 mg cholesterol were used. This mixture was dried in a round-bottom flask in a rotary evaporator. The flask was then placed in a 37°C. water bath and one ml of a 25% trisodium calcium DTPA solution was slowly added to the flask with immediate and constant stirring with a magnetic stirrer. The resultant suspension of liposomes containing DTPA was centrifuged at 2000 revolutions per minute for 5 minutes. The supernatant was carefully pipetted off and the liposome pellet was resuspended in normal saline. The same centrifugation and resuspension procedure was repeated five times to insure the complete removal of nonencapsulated DTPA solution. The liposomes were finally resuspended in saline solution.

The formation of the liposomes was found to be affected by the purity of the phosphatidylcholine used and by the concentration of the electrolyte. Under ideal conditions, the liposomes were small, usually less than 10 microns, and usually spherical and well separated from each other. When liposomes were prepared with partially degraded phosphatidylcholine, fewer liposomes were formed, and clusters of liposomes instead of single, separate liposomes were observed. However, when the phosphatidylcholine was purified, as by thin layer chromatography, within a week before use, spherical, single, well-separated liposomes were consistently obtained. When the concentration of EDTA was higher than 10 percent, fewer liposomes were formed. Consequently, it is preferred that EDTA liposomes be prepared with highly purified, fresh phosphatidylcholine and EDTA solutions at concentrations between 5 and 10 percent. When partially degraded or impure phosphatidylcholine was used to make liposomes containing DTPA, some of these liposomes were as large as 80 microns in diameter, and large clusters of liposomes were observed. Successful liposome formation can be achieved with a 25% trisodium calcium DTPA.

The encapsulation of chelating agents by the liposomes, i.e. within the artificial lipid spherules, was verified by use of radioactive tagged chelating agents. Using the above-described preparation technique, $^{45}$Ca-DTPA and $^{14}$C-EDTA were used in place of the usual electrolyte. Following extensive washing of the liposomes produced in accordance with the technique, the labeled chelating agents were found within the liposomes.

The uptake and retention by the body and cells of the liposome encapsulated chelating agent was studied by use of the radio-labelled chelating agents prepared in accordance with the technique described above. Distribution of injected $^{14}$C-EDTA liposomes was studied in mice and compared with that of free $^{14}$C-EDTA to determine the delivery of the chelating agent to the various organs and retention of the so-introduced chelating agent over a period of time. The results of these studies are indicated in Table I and Table II below.

TABLE I

DISTRIBUTION AND RETENTION OF $^{14}$C-EDTA ENCAPSULATED IN LIPOSOMES

| Time after injection | Brain | Blood | Kidneys | Liver | Spleen | Lungs | Total in tissues shown |
|---|---|---|---|---|---|---|---|
| 5 min | 0.616±0.223 | 27.642±2.722 | 1.954±0.271 | 24.602±5.577 | 3.179±0.133 | 37.851±2.836 | 95.843±1.065 |
| 15 min | 0.343±0.026 | 8.450±2.167 | 1.288±0.083 | 38.667±3.508 | 8.188±1.478 | 25.674±2.658 | 82.611±1.063 |
| 1 hour | 0.283±0.034 | 2.418±0.619 | 0.630±0.059 | 37.353±4.722 | 18.030±2.505 | 13.601±3.482 | 72.316±4.600 |
| 6 hours | 0.257±0.039 | 1.001±0.240 | 0.446±0.019 | 40.981±1.833 | 11.454±1.233 | 9.862±0.566 | 64.002±1.500 |
| 12 hours | 0.163±0.023 | 0.468±0.059 | 0.443±0.032 | 38.845±4.746 | 6.709±0.965 | 7.636±0.562 | 54.263±4.155 |
| 18 hours | 0.185±0.016 | 0.915±0.104 | 0.428±0.038 | 26.169±4.701 | 9.275±2.100 | 8.374±0.453 | 45.347±2.333 |
| 1 day | 0.237±0.021 | 0.544±0.065 | 0.363±0.021 | 24.137±2.263 | 11.305±0.806 | 7.127±0.530 | 43.712±1.275 |
| 2 days | 0.124±0.018 | 0.757±0.210 | 0.348±0.028 | 20.946±1.235 | 6.791±1.280 | 4.670±0.529 | 33.636±2.117 |
| 3 days | 0.107±0.006 | 0.803±0.025 | 0.305±0.036 | 9.387±0.749 | 7.003±0.452 | 3.601±0.748 | 21.206±0.433 |
| 7 days | 0.052±0.007 | 0.463±0.152 | 0.162±0.019 | 3.794±1.173 | 1.315±0.128 | 0.291±0.102 | 6.078±1.182 |
| 17 days | 0.030±0.006 | 0.330±0.042 | 0.060±0.007 | 0.731±0.365 | 0.142±0.039 | 0.066±0.022 | 1.359±0.429 |

TABLE II

DISTRIBUTION AND RETENTION OF NONENCAPSULATED $^{14}$C-EDTA

| Time after injection | Brain | Blood | Kidneys | Liver | Spleen | Lungs | Total in tissues shown |
|---|---|---|---|---|---|---|---|
| 5 min | 0.157±0.018 | 13.218±0.515 | 7.134±0.826 | 1.802±0.101 | 0.215±0.012 | 0.663±0.054 | 23.189±1.299 |
| 15 min | 0.090±0.020 | 5.024±0.673 | 2.681±0.176 | 0.972±0.041 | 0.103±0.001 | 0.337±0.024 | 9.208±0.880 |
| 1 hour | 0.055±0.006 | 0.917±0.153 | 0.355±0.028 | 0.394±0.012 | 0.033±0.007 | 0.041±0.003 | 1.795±0.151 |
| 6 hours | 0.043±0.003 | 0.560±0.160 | 0.165±0.019 | 0.316±0.045 | 0.036±0.007 | 0.031±0.008 | 1.151±0.206 |
| 1 day | 0.034±0.003 | 0.602±0.144 | 0.077±0.005 | 0.326±0.039 | 0.042±0.004 | 0.041±0.010 | 0.971±0.202 |
| 3 days | 0.034±0.003 | 0.040±0.010 | 0.061±0.003 | 0.222±0.016 | 0.028±0.003 | 0.028±0.003 | 0.374±0.023 |

Table I shows distribution and retention in mouse tissues of $^{14}$C-EDTA encapsulated in liposomes at various times following intravenous injection. For the liposome-encapsulated $^{14}$C-EDTA study, a total of 44 female CF No. 1 (Carworth Farms) mice, 93 days of age and with a mean weight of 27.0 grams, were used. Each mouse received a single injection, via a tail vein, of $^{14}$C-EDTA liposomes (about 90,000 cpm, in a volume of 0.40 ml). Groups of mice were sacrificed from 5 minutes to 17 days after injection by an intravenous injection of an anesthetic dose of sodium pentobarbital, followed by exsanguination. Samples of blood and various tissues were removed for $^{14}$C-radioactivity determinations. The values in the blood column reflect activity in the estimated blood volume, 2 cm$^3$, as calculated from two 100-microliter samples from each mouse. Values are mean percent of injected $^{14}$C-radioactivity ± the standard error of the mean. Each group contains 4 mice, except those at 5 and 15 minutes (3 mice each) and at 12 hours (5 mice). The liposomes were made from phosphatidylcholine and cholesterol in a 3 to 1 ratio. The liposomes were filtered once through a 1.2 μm Millipore filter.

Table II shows distribution and retention in mouse tissues of nonencapsulated $^{14}$C-EDTA at various times following intravenous injection. For the nonencapsulated $^{14}$C-EDTA study, a total of 24 mice, of the same age and weight as those used for $^{14}$C-EDTA liposomes, were given an injection of a 5% $^{14}$C-labeled CaNa$_2$ EDTA solution (pH 7.4). The activity and volume injected and the route of injection were as described above. Groups of 4 mice each were sacrificed from 5 minutes to 3 days after injection as above. The values shown are, as in Table I, for mean percent of injected $^{14}$C-radioactivity from 4 mice ± the standard error of the mean.

It can be seen from Table II that free $^{14}$C-EDTA was swept from the body quite rapidly, whereas from Table I it can be seen that the liposome encapsulated EDTA remained in the body for a substantial period of time. This is indicative of the fact that the liposome encapsulated EDTA was taken up by the cells. A substantial amount of the liposomes deposited in the liver, the liver containing about 41 percent of the total injected liposome at 6 hours after injection. The labeled chelating agent subsequently transferred out of the liver, at 3 days there being less than 10 percent remaining, and at 17 days less than 1 percent.

Since injected liposomes in the liver have been found to be primarily associated with lysosomes, intracellular organelles responsible for the storage and digestion of incorporated foreign materials, and since colloidal plutonium is also specifically localized in liver lysosomes, the encapsulation of chelating agent provides a means for removing the intracellularly deposited plutonium. In accordance with the present techniques, a chelating agent, in this case DTPA being used in view of the greater complexing ability of the DTPA with plutonium, was encapsulated in liposomes, and the liposome encapsulated DTPA suspended in a saline solution for injection. The suspension can be introduced to the body through intravenous injection, whereby the liposomes will deposit in various organs and, in particular, will be directed toward the liver. The liposomes can transfer across cellular membranes in the liver, thereby gaining access to the interior of the cells. Once in the cells, the lysosomal enzymes will break down the liposomes, releasing the DTPA chelating agent to the interior of the cell. The chelating agent will complex toxic heavy metal, plutonium, and the complexed heavy metal, its ionic charge much lower in comparison with either the toxic metal or the chelating ion itself, can diffuse back across the cell membrane out of the cell. After transferring across the membrane from the cell, the complexed ion will be removed from the body by normal body processes.

Experiments were conducted on mice showing the removal of toxic heavy metals from the body by treatment with liposome encapsulated DTPA.

In experiment 1, 25 female CF No. 1 (Carworth Farms) mice, 60 days of age with a mean weight of 25.7 grams, were given a single intravenous injection of a midrange polymeric plutonium preparation which was 24 percent unfiltrable. Each mouse received 0.4 μcurie of $^{239}$Pu per kilogram of body weight. Separate groups of five mice were treated twice at 3 and 6 days after administration of the plutonium with one of the following: (1) saline solution, (2) nonencapsulated DTPA, (3) liposome encapsulated DTPA, or (4) both encapsulated and nonencapsulated DTPA. The mice were sacrificed at day 10 after plutonium injection, i.e. day 4 after the second therapy.

In experiment 2, 70 female B6CF$_1$ mice were used, since CF No. 1 mice were not available at that time. These mice were 82 days of age with a mean weight of 20.4 grams and were given a single intravenous injection of a midrange polymeric plutonium preparation which was 35 percent unfiltrable. Each mouse received 0.9 μcurie of $^{239}$Pu per kilogram. Separate groups of 4 or 5 mice were given the four different treatments used in experiment 1, but only once, at 3 days after injection of plutonium. Groups of 4 or 5 mice were sacrificed at the following intervals after the single treatment: 6 hours, 1 day, 3 days, and 7 days (i.e. 3 ¼, 4, 6, and 10 days after administration of plutonium). An additional group of 5 mice received liposome encapsulated DTPA twice, at both 3 and 6 days after plutonium administration, and were sacrificed at day 10.

Conventional nonencapsulated DTPA was given by intraperitoneal injection for convenience. It has been established that intraperitoneal and intravenous injections of DTPA give identical results in plutonium therapy. A dose of 100 mg of DTPA per kilogram of body weight was given at each injection in both experiments 1 and 2. The liposome encapsulated DTPA was injected intravenously at a dose of 2 mg of DTPA per mouse (about 80 mg/kg in experiment 1 and 100 mg/kg in experiment 2). It was injected within 3 hours of its preparation in experiment 1 and within 1 to 2 days in experiment 2. Tissues from the individual mice and (in experiment 2 only) the separated urine and feces from pairs of mice were ashed and assayed for $^{239}$Pu content.

The diameters of liposomes from separate preparations, roughly determined by dark-field photomicrography, were found to vary between 1 and 10 microns. When mixed in vitro with mouse blood, the liposomes were unchanged morphologically and did not aggregate for at least 2 hours.

Figure 2:
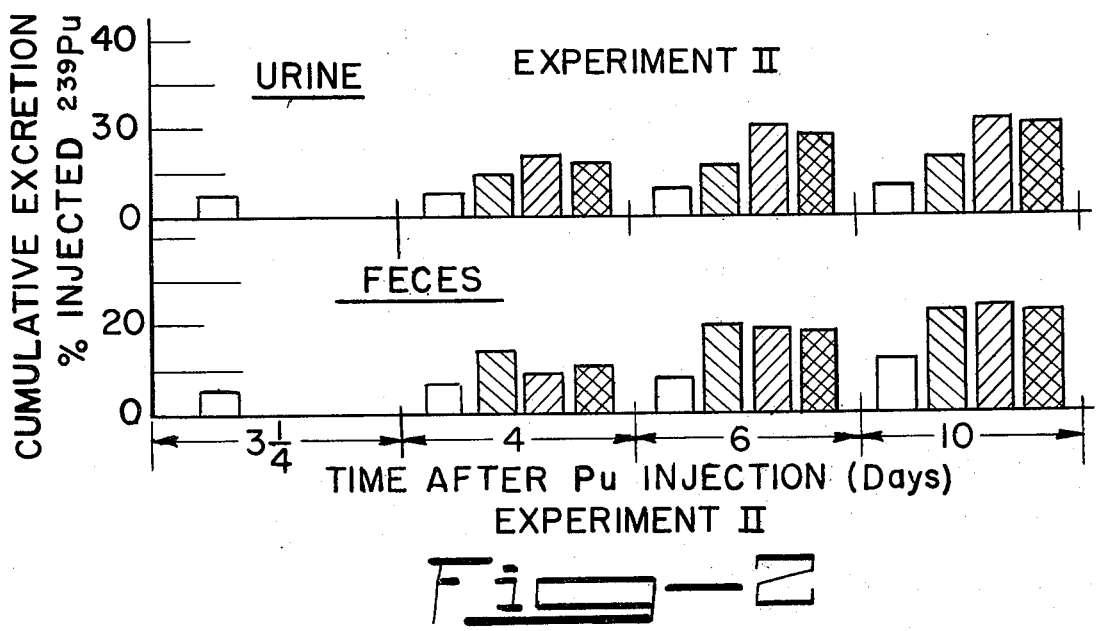
FIG. 2 graphically illustrates the cumulative amount of $^{239}$Pu excreted over increasing periods of time following various treatments.

The liposome encapsulated DTPA given alone consistently reduced the level of plutonium in the liver below that achieved by conventional nonencapsulated DTPA therapy. This is indicated from the results as shown in the graph of FIG. 1. FIG. 1 shows the percent of injected $^{239}$Pu in liver of mice after various treatments: a) saline solution, b) conventional nonencapsulated DTPA, c) liposome encapsulated DTPA, d) both encapsulated and nonencapsulated DTPA. In experiment 1, each treatment was given at 3 days and again at 6 days after injection of plutonium. In experiment 2, treatment was given at 3 days only. As can be seen, liposome encapsulated DTPA not only removed the essentially extracellular fraction of plutonium which can be removed by conventional DTPA, but it also removed an additional intracellular fraction. In experiment 1 at 10 days after plutonium administration, two injections of liposome encapsulated DTPA removed 37 percent of the intracellular plutonium while the combined therapy removed 45 percent. In experiment 2, removal of intracellular plutonium at 6 and 24 hours after a single injection of liposome encapsulated DTPA was not significant; but at 3 and 7 days after therapy, about 20 percent was removed. There was no additional removal of intracellular plutonium in the group of 5 mice given two injections of liposome encapsulated DTPA. Therefore, the greater removal of intracellular plutonium observed in experiment 1 was probably not due to the second injection of liposome encapsulated DTPA. Analysis of urine and feces in experiment 2, the results of which are graphically illustrated in FIG. 2 which shows the cumulative $^{239}$Pu excretion in the urine and feces of mice given various treatments a single time 3 days after plutonium injection, showed that the mice treated with liposome encapsulated DTPA had a significantly higher urinary excretion of plutonium than the mice receiving conventional DTPA therapy. The magnitude of this increase indicates that liposome encapsulated DTPA removed additional plutonium from tissues other than the liver. This additional urinary plutonium appears to be from the skeleton. The plotonium burden in the skeleton (calculated as the content of both femurs multiplied by a factor of 13) of mice receiving liposome encapsulated DTPA was lower by about 5 percent of the injected dose of plutonium compared to that of mice receiving conventional DTPA therapy.

Since plutonium in the liver is found intracellularly in lysosomes, and injected liposomes are also associated with lysosomes of liver cells, the results indicate that liposome encapsulated DTPA has removed part of the intracellular plutonium from the liver. The greater removal of plutonium from the liver by liposome encapsulated DTPA in experiment 1 than in experiment 2 is probably due to a higher intracellular deposition of plutonium. The mice in experiment 1 apparently received a more colloidal preparation of plutonium than those in experiment 2 as judged by the greater amount in the liver. Colloidal plutonium seems to be deposited intracellularly in the liver to a greater extent than noncolloidal plutonium. These results demonstrate that a chelating agent encapsulated within liposomes removes an additional fraction of plutonium from the liver that is not removed by conventional DTPA therapy.

Other similar experiments were conducted with $^{198}$Au, the results of which showed increased excretion of the $^{198}$Au with liposome encapsulated DTPA as compared with excretion by free DTPA or saline. It is further believed that other toxic heavy metals, such as mercury, lead, yttrium and cerium, which can be complexed by chelating agents will similarly be removed by liposome encapsulated chelating agents.

The embodiments of the invention in which an exclusive property or privilege is claimed are defined as follows:

1. A method of transferring a polyaminopolycarboxylic acid chelating agent across a cellular membrane comprising: encapsulating said polyaminopolycarboxylic acid chelating agent within liposomes; and carrying said liposome encapsulated chelating agent to said cellular membrane, whereby said liposome encapsulated chelating agent will transfer across said cellular membrane.

2. A method of introducing a polyaminopolycarboxylic acid chelating agent into the interior of a cell in accordance with the method of claim 1 wherein said cellular membrane is the membrane wall of said cell and said encapsulated chelating agent passes through the membrane wall of said cell into the interior of said cell, wherein said liposomes will be decomposed, thereby releasing said polyaminopolycarboxylic acid chelating agent to the interior of said cell.

3. The method in accordance with claim 2 wherein said cell is a cell of a living organism and said encapsulated chelating agent is carried to said cell by injecting a saline suspension of said liposome encapsulated chelating agent into the blood stream of said living organism whereby said encapsulated chelating agent is carried to the cell within the blood.

4. A method for the removal of intracellularly deposited toxic heavy metals comprising:
   encapsulating a polyaminopolycarboxylic acid chelating agent within liposomes;
   introducing said liposome encapsulated chelating agent into the blood system by intravenous injection; whereby
   said liposome encapsulated chelating agent is carried to said body cells within said blood system;
   said liposome encapsulated chelating agent is passed through the cell wall into the interior of said body cell;
   said polyaminopolycarboxylic acid chelating agent is released to the interior of said cell by the biological degradation of said liposome by lysosomal enzymes, said released chelating agent complexing said intracellularly deposited toxic metal;
   said complexed toxic metal is passed through the cell wall into said blood stream; and
   said complexed toxic metal is removed from said blood stream and the body by normal body processes.

5. The method in accordance with claim 4 wherein said liposomes are prepared from a mixture of lecithin and cholesterol.

6. The method in accordance with claim 4 wherein said polyaminopolycarboxylic acid chelating agent is chosen from the group consisting of EDTA and DTPA.

7. The method in accordance with claim 6 wherein said toxic heavy metals are selected from the group consisting of plutonium, gold, mercury, and lead.

8. A method in accordance with claim 6 wherein encapsulated DTPA is prepared from a solution of trisodium calcium DTPA.

9. A therapy method for toxic heavy metal poisoning comprising: encapsulating a polyaminopolycarboxylic acid chelating agent within liposomes; forming a saline solution containing nonencapsulated polyaminopolycarboxylic acid chelating agent and a suspension of the liposome encapsulated chelating agent; introducing said saline suspension into the blood stream by intravenous injection; whereby said chelating agent will complex said free toxic heavy metals and said encapsulated chelating agent will enter body cells and combine with intracellularly deposited toxic heavy metals and whereby said complexed toxic heavy metals will be passed from the body by normal body processes.

* * * * *